(12) United States Patent
Zaiken et al.

(10) Patent No.: US 8,663,174 B2
(45) Date of Patent: Mar. 4, 2014

(54) HUB ASSEMBLY HAVING A HIDDEN NEEDLE FOR A DRUG DELIVERY PEN

(75) Inventors: Eliot Zaiken, Sparta, NJ (US); Keith N. Knapp, Warwick, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 405 days.

(21) Appl. No.: 12/618,242

(22) Filed: Nov. 13, 2009

(65) Prior Publication Data

US 2011/0118667 A1    May 19, 2011

(51) Int. Cl.
*A61M 5/00* (2006.01)

(52) U.S. Cl.
USPC .......................... 604/198; 604/110; 604/192

(58) Field of Classification Search
USPC ......... 604/110, 138, 162, 181, 187, 192, 197, 604/198
See application file for complete search history.

(56) References Cited

U.S. PATENT DOCUMENTS

| | | | |
|---|---|---|---|
| 4,994,045 A * | 2/1991 | Ranford | 604/198 |
| 5,472,430 A | 12/1995 | Vaillancourt et al. | |
| 5,746,727 A | 5/1998 | Graves | |
| 5,964,731 A | 10/1999 | Kovelman | |
| 6,547,764 B2 | 4/2003 | Larsen | |
| 6,773,415 B2 | 8/2004 | Heiniger | |
| 6,855,129 B2 | 2/2005 | Jensen | |
| 6,872,194 B2 * | 3/2005 | Doyle et al. | 604/192 |
| 6,884,237 B2 * | 4/2005 | Asbaghi | 604/198 |
| 6,986,760 B2 * | 1/2006 | Giambattista et al. | 604/198 |
| 7,211,069 B2 | 5/2007 | Lehmann | |
| 7,384,414 B1 | 6/2008 | Marshall | |
| 7,462,168 B2 | 12/2008 | Stonehouse | |
| 7,540,858 B2 | 6/2009 | DiBiasi | |
| 7,666,164 B2 | 2/2010 | Giambattista | |
| 2007/0106225 A1 | 5/2007 | Millerd | |
| 2011/0066114 A1 | 3/2011 | McDown. | |
| 2011/0118667 A1 | 5/2011 | Zaiken | |
| 2011/0160675 A1 | 6/2011 | Ruan | |

FOREIGN PATENT DOCUMENTS

| | | |
|---|---|---|
| FR | 2884723 | 10/2006 |
| WO | 03066141 | 8/2003 |
| WO | 2007077463 | 7/2007 |

* cited by examiner

*Primary Examiner* — Laura Bouchelle
(74) *Attorney, Agent, or Firm* — Roylance, Abrams, Berdo & Goodman, L.L.P.

(57) ABSTRACT

A hub assembly for a pen injection device allows a needle to be disposed in at least one of a plurality of positions prior to an injection. A hub of the hub assembly is connected to the pen injection device, and the needle is received by the hub. A shield is movably connected to the hub and allows the needle to be disposed in at least one of several positions prior to an injection, such as a position in which the needle is visible for priming and a position that prevents the needle from being visible. A tab connected to the hub is received by a channel formed in the shield to control movement of the shield.

16 Claims, 6 Drawing Sheets

HUB ASSEMBLY HAVING A HIDDEN NEEDLE FOR A DRUG DELIVERY PEN

FIELD OF THE INVENTION

The present invention relates to a hidden needle for a pen injection device. More particularly, the present invention relates to a shield connected to a hub of the pen injection device that covers the needle to prevent a patient from seeing the needle during an injection. Still more particularly, the present invention relates to a shield having a plurality of positions that allows a user to observe the needle being primed and prevents the patient from seeing the needle during an injection.

BACKGROUND OF THE INVENTION

Medication delivery pens are hypodermic syringes used for self-injection of precisely measured doses of medication. Pens are widely used, for example, by diabetics to dispense insulin.

A typical prior art medication delivery pen includes a cartridge which contains a volume of liquid medication sufficient for several doses. The dose is injected into a tissue area, such as the intramuscular tissue layer, the subcutaneous tissue layer, or the intradermal tissue layer.

The assembly and operation of a typical pen injection device, as shown in FIGS. 1 and 2, is described in U.S. Patent Application Publication No. 2006/0229562, published on Oct. 12, 2006, which is hereby incorporated by reference in its entirety.

Pen injection devices, such as the exemplary pen injector 100, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location.

FIG. 2 is an exploded view of an exemplary drug delivery pen shown in FIG. 1. The dose knob/button 24 has a dual purpose and is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used such as attaching to the cartridge. To protect a user, or anyone who handles the pen injection device 100, an outer shield 69, which attaches to the hub 20, covers the hub. An inner shield 59 covers the patient needle 11 within the outer shield 69. The inner shield 59 can be secured to the hub 20 to cover the patient needle 11 by any suitable means, such as an interference fit or a snap fit. The outer shield 69 and inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18, but does not move with respect to the medicament cartridge 12. The stopper 15 is axially displaceable within the medicament cartridge 12 while maintaining a fluid tight seal.

The outer shield 69 and the inner shield 59 are removed from the hub 20 and needle 11 prior to injecting a patient with the medicament stored in the cartridge 12. Some patients become uncomfortable at the sight of the needle 11, which is visible prior to the injection. Accordingly, a need exists for a pen injection device having a hub assembly that prevents a patient from seeing the needle prior to an injection.

SUMMARY OF THE INVENTION

In accordance with an aspect of the present invention, a hub assembly for a pen injection device has a shield to prevent a patient from seeing the needle prior to an injection.

In accordance with another aspect of the present invention, the shield has a plurality of positions such that the needle can be visible for priming prior to the injection.

The hub assembly for a pen injection device according to an exemplary embodiment of the present invention prevents a user from seeing the needle prior to the injection. A hub is connected to the pen injection device. A needle is received by the hub. A shield is movably connected to the hub such that the needle is not visible prior to the injection.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components and structures.

DETAILED DESCRIPTION OF THE EXEMPLARY EMBODIMENTS

Figure 1:
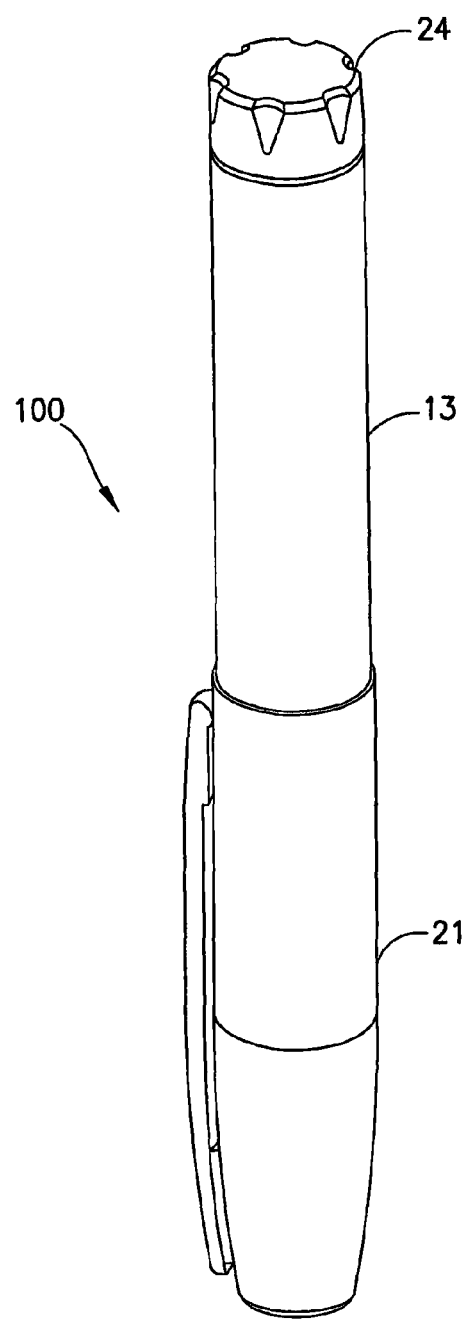
FIG. 1 is a perspective view of an assembled existing pen needle assembly.

In an exemplary embodiment of the present invention, as shown in FIGS. 3-10, a hub assembly 101 for a pen injection device 100 (FIG. 2) prevents a patient from seeing a needle 103 of the hub assembly during the injection. A hub 111 of the hub assembly 101 is connected to the pen injection device. The needle 103 is received by the hub 111. A shield 131 is movably connected to the hub such that the needle is not visible during the injection.

Figure 6:
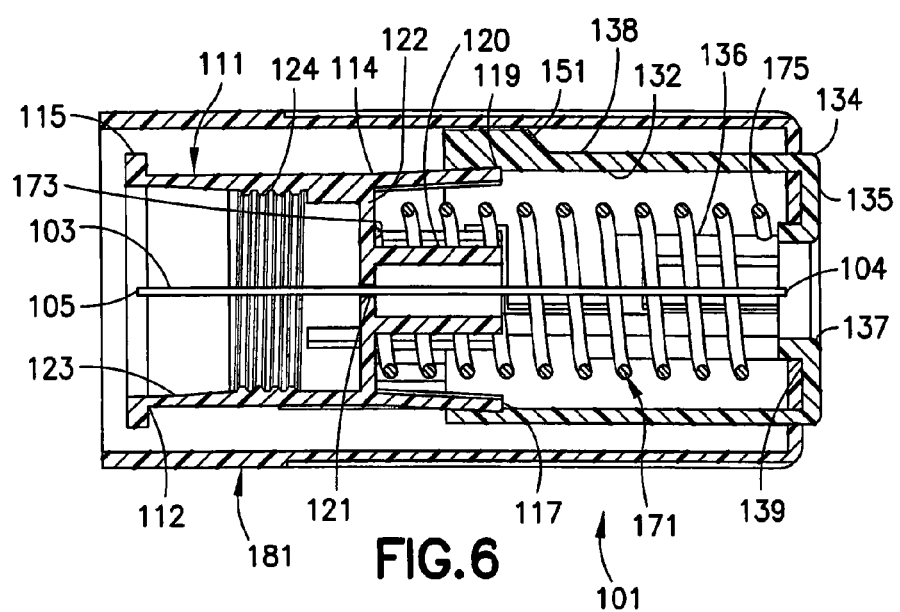
FIG. 6 is an elevational view in partial cross section of the hub assembly of FIG. 3.

The hub 111 has a body 113, which preferably has a cylindrical shape, having a first end 112 and a second end 114. A flange 115 extends outwardly from the first end 112 of the hub body 113. A substantially planar base 122 is formed at the second end 114 of the hub body 113. A plurality of flexible arms 116-119 extend outwardly from base 122 at the second end 114 of the hub body 113. Preferably, the diameter at the free end of the flexible arms 116-119 is larger than a diameter of the base 122 of the hub body, as shown in FIG. 6.

A hub post 120 extends from the base 122 at the second end 114 of the hub body 113. Preferably, the hub post 120 is hollow, as shown in FIG. 6, to receive the needle 103 and an adhesive to secure the needle therein. An opening 121 in the base 122 allows the needle 103 to pass through to the first end 112 of the hub 111, such that when the hub 111 is connected to the pen injection device the needle is in fluid communication with the medicament stored in the cartridge. An inner surface 123 of the hub 111 has a threaded portion 124 to facilitate connecting the hub to the pen injection device. A distal end 105 of the needle pierces the septum 16 (FIG. 2) when the hub 111 is threadably engaged with the pen injection device to put the needle in fluid communication with the cartridge 12.

Figure 7:
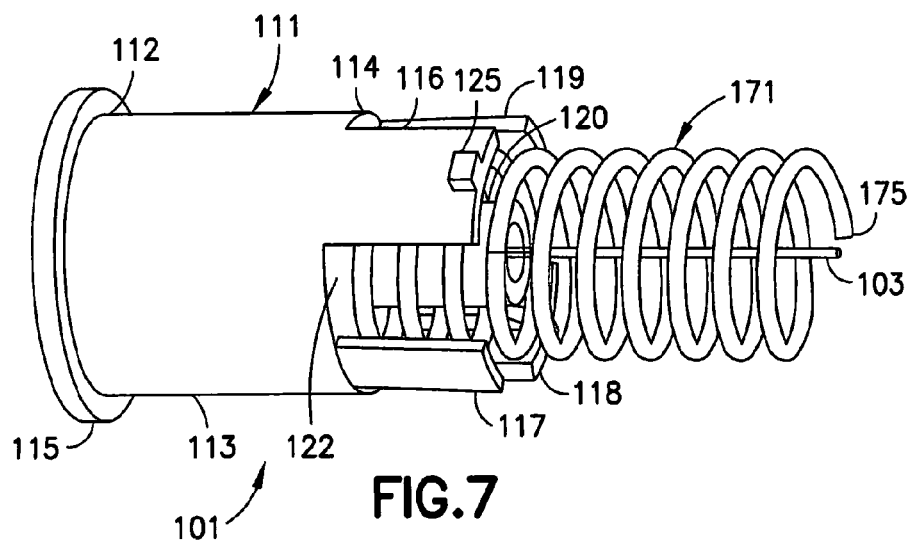
FIG. 7 is a perspective view of the hub of the hub assembly of FIG. 3.

As shown in FIG. 7, the hub 111 preferably has four flexible arms 116-119. Arms 116 and 118 are preferably diametrically opposed and arms 117 and 199 are preferably diametrically opposed, although other configurations may be used. Flexible arm 116 has a tab 125 extending outwardly therefrom and flexible arm 118 can have a similar tab (not shown) extending therefrom.

The shield 131 is disposed over the hub 111. The flexible arms 116-119 engage an inner surface 132 of the shield 131, thereby creating an interference fit to securely retain the shield on the hub 111. A post 136 extends inwardly from an inner surface 139 of the base 135 of the shield. A first end 130 of the shield 131 limits axial movement of the hub 111 during an injection. An opening 137 in the base 135 allows the needle 103 to pass therethrough during an injection. Wings 151 and 152 may extend outwardly from an outer surface 138 of the shield 131 to facilitate gripping the shield by a user, and preferably wings 151 and 152 are diametrically opposed.

The tabs 125 of the hub 111 are received by a channel 141 in the shield 131 to allow movement between the hub and shield. The channel 141 preferably has four sections. A first axial section 143 extends axially from proximal a first end 133 of the shield 131 to a second end 134. A first circumferential section 145 extends circumferentially from an end of the first axial section 143. A second circumferential section 147 extends circumferentially from the first axial section 143 and is preferably substantially parallel to the first circumferential section 145. A second axial section 149 extends from an end of the second circumferential section 149 and is preferably parallel to the first axial section 143. Preferably, a second channel is diametrically opposed from the first channel 141.

Figure 9:
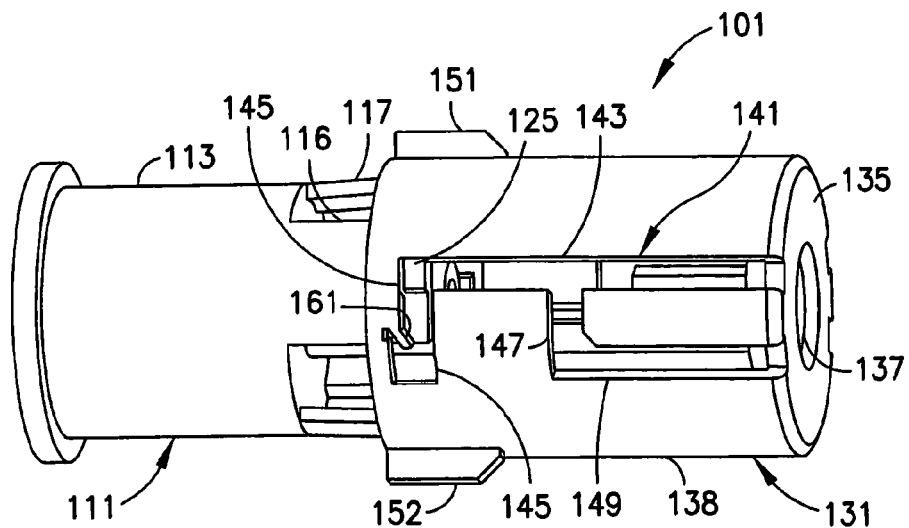
FIG. 9 is a perspective view of the hub assembly of FIG. 3 in which the needle is hidden.
Figure 10:
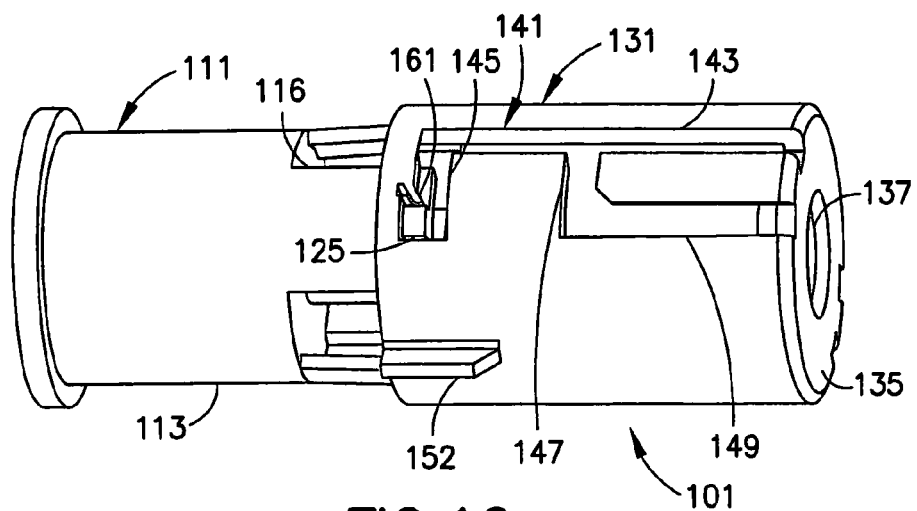
FIG. 10 is a perspective view of the hub assembly of FIG. 3 in a locked position.

A flexible finger 161 extends into the first circumferential section 145 away from the first axial section 143. When the tab 125 is disposed in the first circumferential section 145 and the shield is rotated circumferentially such that the tab 125 passes over the flexible finger 161, as shown in FIGS. 9 and 10, the flexible finger 161 prevents the tab 125 from passing back over the flexible finger. Thus, the shield 131 is locked on the hub 111 such that the needle is prevented from being moved out of the shield 131. Other suitable means may be used to lock and prevent the needle 103 from moving out of the shield 131.

A spring 171, or other suitable biasing means, is disposed between the hub 111 and the shield 131, as shown in FIGS. 3, 4, 6 and 7. The spring 171 has a first end 173 that abuts the base 122 of the hub 111, and the spring surrounds the hub post 120. The spring 171 has a second end 175 that abuts an inner surface 139 of the base 135 of the shield 131 and surrounds the shield post 136. The spring biases the shield 131 to a position, as shown in FIG. 6, that shields the proximal end 104 of the needle from a patient's view, in addition to providing tension to maintain the connection between the hub 111 and the shield 131.

An outer cover 181, as shown in FIG. 6, may be disposed over the hub assembly 101 to cover the hub 111 and the shield 131. The outer cover 181 may be connected to the hub assembly 101 in any suitable manner, such as by an interference fit. The outer cover 181 is removed prior to performing an injection.

Figure 2:
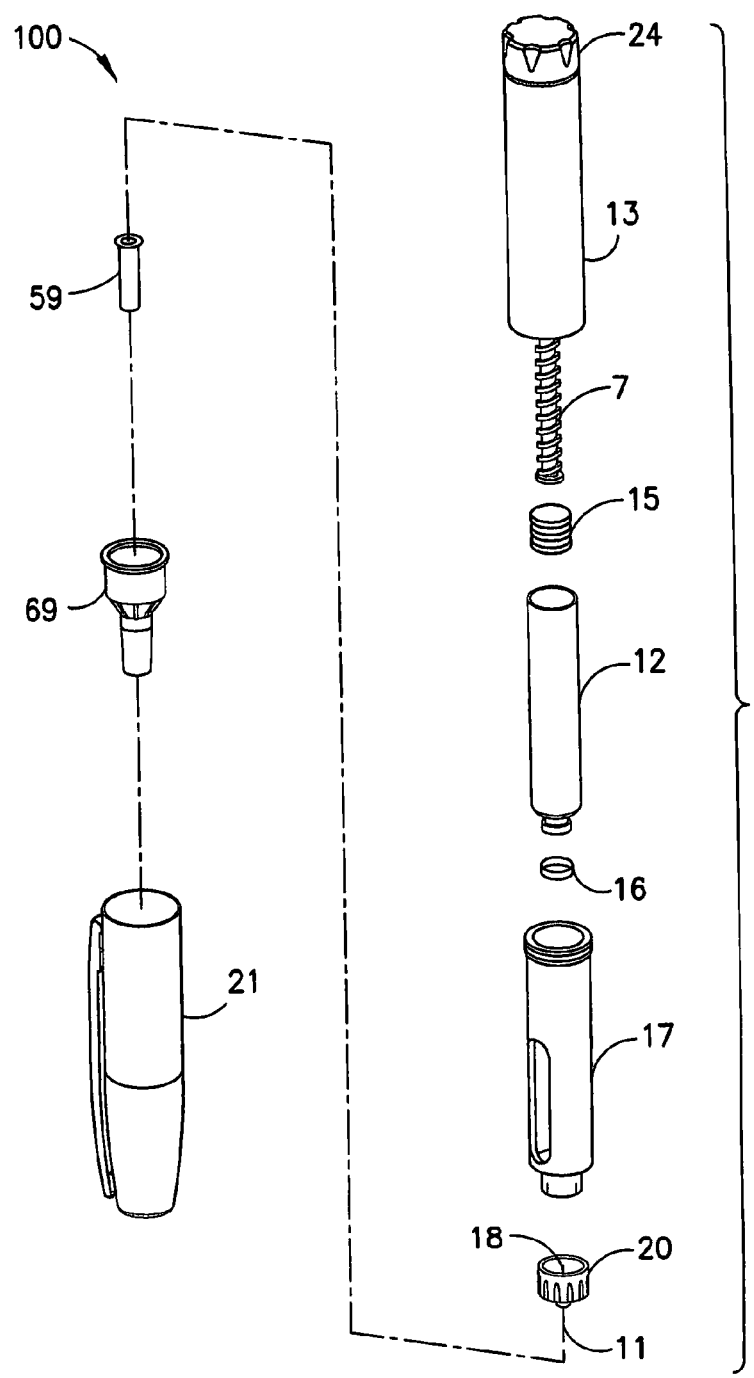
FIG. 2 is an exploded perspective view of the components of the pen needle assembly of FIG. 1.
Figure 3:
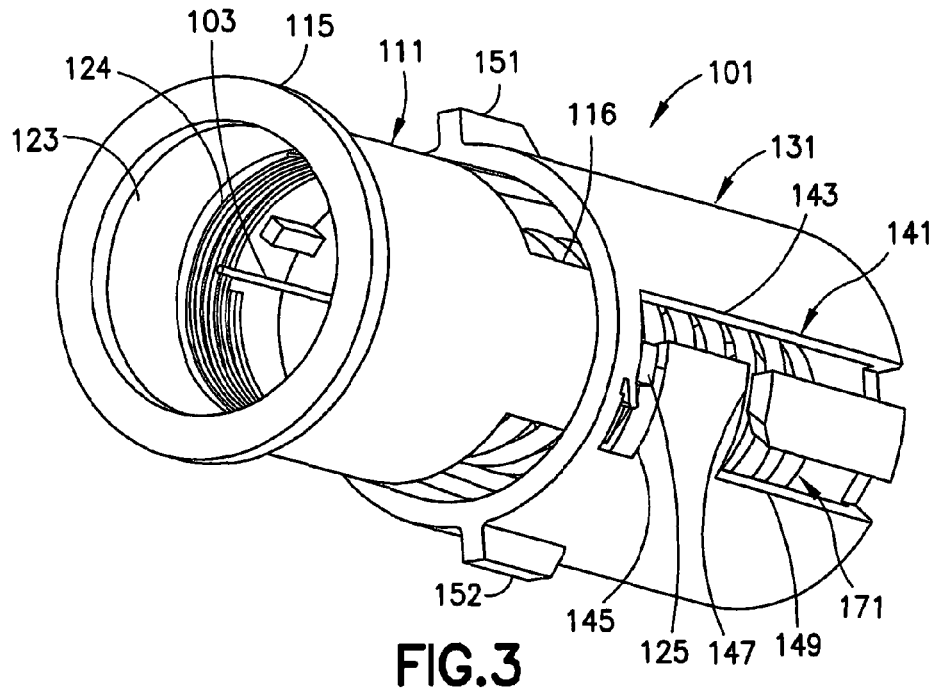
FIG. 3 is a perspective view of a hub assembly according to an exemplary embodiment of the present invention.
Figure 4:
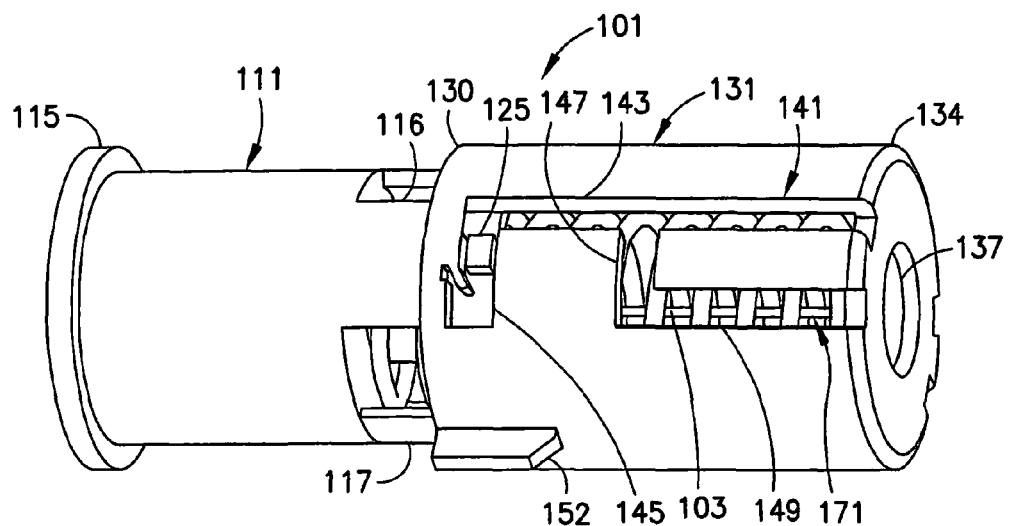
FIG. 4 is a perspective view of the hub assembly of FIG. 3.
Figure 5:
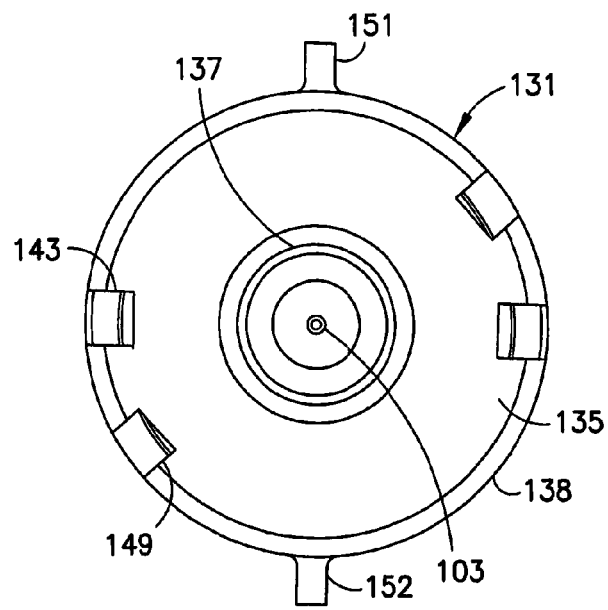
FIG. 5 is an end elevational view of the hub assembly of FIG. 3.

When an injection is to be made, the hub assembly 101 is threadably engaged with a pen injection device 100 (FIG. 2). The distal end 105 of the needle 103 pierces the septum 16 (FIG. 2) such that the needle is in fluid communication with the cartridge 12 (FIG. 2). The outer cover 181 is then removed to expose the hub 111 and the shield 131. Preferably, the tab 125 is initially in a position as shown in FIGS. 3 and 4 that provides a temporary lock. The walls of the first circumferential channel 145 block axial movement of the shield 131, thereby providing a temporary locking position in which accidental movement of the needle 103 and accidental needle sticks are prevented. In this position, a patient is not able to see the needle 103. However, the tab 125 may be initially positioned at any suitable position in the channel 141.

Figure 8:
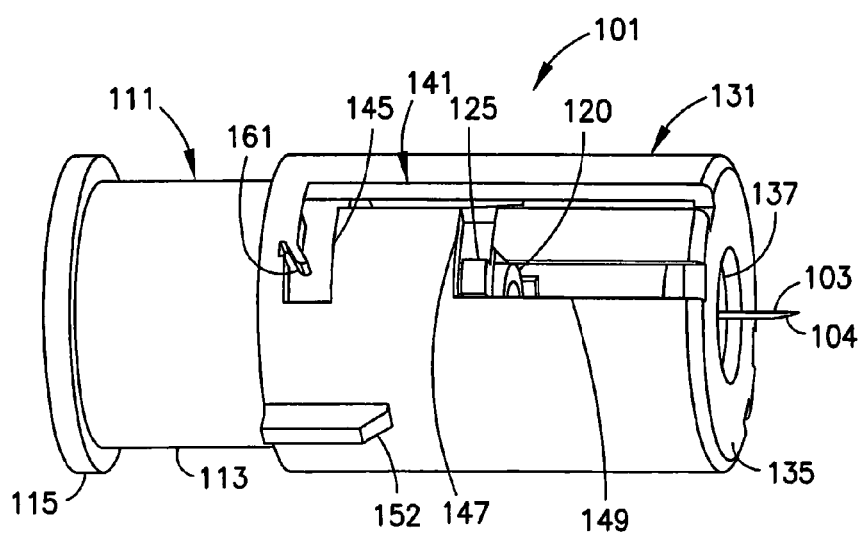
FIG. 8 is a perspective view of the hub assembly of FIG. 3 in which the needle is in a priming position.

In one method of priming the needle 103, as shown in FIG. 8, the shield 131 is rotated to move the tab 125 to the first axial channel 143, as shown in FIG. 9. Wings 151 and 152 on the shield 131 facilitate gripping and moving the shield. The shield 131 is then moved axially toward the hub flange 115 until the tab 125 is aligned with the second circumferential channel 147 and the shield is rotated such that the tab 125 is at the intersection of the second circumferential channel 147 and the second axial channel 149. The proximal end 104 of the needle is then barely visible through the opening 137 such that the user can visibly see medicament droplets to ensure proper priming of the needle. The position of the proximal end 104 of the needle 103 is exaggerated in FIG. 8 for descriptive purposes, and the proximal end of the needle is barely visible through the opening 137 in the priming position, such that a patient would not be made to feel uncomfortable. However, the position of the second circumferential section 147 relative to the base 135 of the shield 131 can be adjusted such that the proximal end 104 of the needle 103 extends beyond the base 135 of the shield 131. In many instances this could be desirable, for example, a health care provider who wants to verify the priming process.

To perform the injection, the base 135 of the shield 131 is placed on the injection site and the hub 111 is pushed toward the injection site such that the tab 125 moves axially in the second axial channel 149. The flange 115 of the hub 111 abuts the distal end 130 of the shield 131 to limit axial movement of the needle, thereby controlling the injection depth.

When priming of the needle 103 is not desired, or after priming has been performed, an injection can be made from the position in which the tab 125 is at the intersection of the first axial channel 143 and the first circumferential channel 145. From the priming position shown in FIG. 8, the shield is rotated circumferentially and then moved axially toward the hub flange 115. The base 135 of the shield 131 is then placed on the injection site and the hub 111 is pushed toward the injection site such that the tab 125 moves axially in the first axial channel 143. The flange 115 of the hub 111 abuts the distal end 130 of the shield 131 to limit axial movement of the needle, thereby controlling the injection depth.

Following an injection, the spring 171 moves the tab 125 rearwardly in one of the axial channels, depending on which channel the tab is located in. To permanently lock the hub assembly 101, the shield 131 is then such that the tab 125 is in the first circumferential channel 145. The shield 131 is rotated until the tab 125 passes over the flexible finger 161, as shown in FIG. 10. The flexible finger 161 flexes inwardly toward the hub flange 115, such that the tab 125 is able to move to the locked position shown in FIG. 10. The tab 125 is prevented from passing over the flexible finger 161 because the flexible finger does not flex outwardly away from the hub flange 115, such that movement of the tab over the flexible finger is prevented.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A hub assembly for a pen injection device, comprising:
a hub for connecting to the pen injection device;
a needle received by said hub;
a shield movably connected to said hub such that said shield is positionable in at least one of a plurality of positions prior to injection;
a plurality of flexible arms extending outwardly from an end of said hub to engage an inner surface of said shield to create a friction fit therebetween;
a channel formed in said shield;
a tab on at least one of said flexible arms and movably received by said channel, thereby guiding movement of said shield relative to said hub as said tab moves through said channel, said channel having connected first and second substantially parallel axial sections through which said tab is movable and each of said first and second axial sections having first ends preventing further rearward axial movement of said tab therein and second ends for exposing the needle for an injection; and
a flexible finger disposed in said channel such that when said tab passes over said flexible finger said shield becomes locked to said hub and is substantially prevented from moving.

2. The hub assembly of claim 1, wherein
said plurality of flexible arms extend radially outwardly from said hub.

3. The hub assembly of claim 1, wherein
a spring is disposed between said hub and said shield such that said shield is biased to a position covering said needle.

4. The hub assembly of claim 1, wherein
threads are disposed on an internal surface of said hub to threadably engage the pen injection device.

5. The hub assembly of claim 1, wherein
a wing extends outwardly from said shield to facilitate gripping said shield by a user.

6. The hub assembly of claim 1, wherein
an outer cover is removably connected to said hub assembly to cover said hub and said shield.

7. The hub assembly of claim 1, wherein
said channel has a portion substantially perpendicular to a direction in which said needle moves and connecting said first and second axial sections such that when said tab is disposed in said portion of said channel said shield is substantially prevented from being moved.

8. The hub assembly of claim 1, wherein
said second axial section of said channel has a position in which a proximal end of said needle is visible to prime said needle.

9. The hub assembly of claim 1, wherein
said flexible finger flexes to allow movement of said tab in a first direction and resists flexing to prevent movement of said tab past said flexible finger in a second direction opposite to said first direction.

10. The hub assembly of claim 1, wherein
the first end of the first axial channel is disposed axially rearwardly of the first end of the second axial channel.

11. A hub assembly for a pen injection device, comprising:
a hub to connect to the pen injection device;
a needle received by said hub;
a shield movably connected to said hub such that said shield is positionable in at least one of a plurality of positions prior to an injection, a channel being formed in said shield and receiving a tab to control movement of said shield, said channel having connected first and second substantially parallel axial sections through which said tab is repeatedly movable and each of said first and second axial sections having first ends preventing further rearward axial movement of said tab therein and second ends for exposing the needle for an injection;
a plurality of flexible arms extending outwardly from an end of said hub to engage an inner surface of said shield, at least one of said flexible arms having said tab;
a spring disposed between said hub and said shield such that said shield is biased to a position covering said needle; and
a flexible finger disposed in said channel that flexes to allow movement of said tab past said flexible finger in a first direction and resists flexing to prevent movement of said tab past said flexible finger in a second direction opposite to said first direction to lock said shield to said hub to substantially prevent movement of said shield.

12. The hub assembly of claim 11, wherein
said channel has first and second circumferential sections connected to said first axial section, and said second axial section connected to said second circumferential section.

13. The hub assembly of claim 12, wherein
when said tab is positioned at an intersection between said second circumferential section and said second axial section, said needle is in a priming position.

14. The hub assembly of claim 12, wherein
said flexible finger is disposed in said first circumferential section.

15. The hub assembly of claim 12, wherein
when said tab is positioned in said first circumferential section, said shield is prevented from moving axially.

16. The hub assembly of claim 11, wherein
the first end of the first axial channel is disposed axially rearwardly of the first end of the second axial channel.

* * * * *